(12) United States Patent  (10) Patent No.: US 8,649,878 B2
Swoyer  (45) Date of Patent: Feb. 11, 2014

(54) TEMPORARY STIMULATION LEAD WITH POLYMER ELECTRODES AND METHOD OF MANUFACTURE

(75) Inventor: John Swoyer, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 526 days.

(21) Appl. No.: 12/818,207

(22) Filed: Jun. 18, 2010

(65) Prior Publication Data

US 2010/0324638 A1    Dec. 23, 2010

Related U.S. Application Data

(60) Provisional application No. 61/218,498, filed on Jun. 19, 2009.

(51) Int. Cl.
*A61N 1/05* (2006.01)

(52) U.S. Cl.
USPC .......................................................... 607/116

(58) Field of Classification Search
USPC ...................... 600/372–381; 607/116, 121
See application file for complete search history.

(56) References Cited

U.S. PATENT DOCUMENTS

| | | | |
|---|---|---|---|
| 4,530,368 A | | 7/1985 | Saulson et al. |
| 4,541,440 A | | 9/1985 | Parsonnet |
| 5,358,516 A | * | 10/1994 | Myers et al. ................... 607/116 |
| 5,667,615 A | | 9/1997 | Maurer et al. |
| 5,861,023 A | * | 1/1999 | Vachon ........................ 607/121 |
| 5,931,862 A | * | 8/1999 | Carson .......................... 607/120 |
| 5,935,465 A | * | 8/1999 | Cardineau et al. ........ 219/121.69 |
| 6,185,463 B1 | | 2/2001 | Baudino |
| 6,360,130 B1 | | 3/2002 | Duysens et al. |
| 6,671,561 B1 | * | 12/2003 | Moaddeb ....................... 607/120 |
| 6,922,588 B2 | | 7/2005 | Kranz et al. |
| 7,062,310 B2 | * | 6/2006 | Bernhart et al. .............. 600/373 |
| 7,067,765 B2 | * | 6/2006 | Bauer et al. ............. 219/121.69 |
| 7,225,035 B2 | | 5/2007 | Brabec et al. |
| 7,239,922 B1 | * | 7/2007 | Boogaard et al. ............. 607/116 |
| 2005/0288761 A1 | | 12/2005 | Brabec |
| 2006/0142652 A1 | | 6/2006 | Keenan |
| 2007/0100411 A1 | | 5/2007 | Bonde |
| 2007/0255369 A1 | | 11/2007 | Bonde et al. |
| 2009/0187236 A1 | | 7/2009 | Marshall et al. |

FOREIGN PATENT DOCUMENTS

| | | |
|---|---|---|
| DE | 10009830 | 9/2001 |
| WO | 9417852 | 8/1994 |

OTHER PUBLICATIONS

European Search Report, Oct. 1, 2010.

* cited by examiner

*Primary Examiner* — Luther Behringer

(74) *Attorney, Agent, or Firm* — Michael F. Scalise

(57) ABSTRACT

A temporary medical lead in which stimulating electrical energy is transmitted to body tissue through the lead electrodes via ionic conduction within the hydrogel material. The structure of the hydrophilic hydrogel material consists of a porous structure into which conductive salt ions are diffused. In addition the structure of the hydrogel material can be loaded with a single or combination of therapeutic drugs from which is eluted from the electrode's surface.

21 Claims, 8 Drawing Sheets

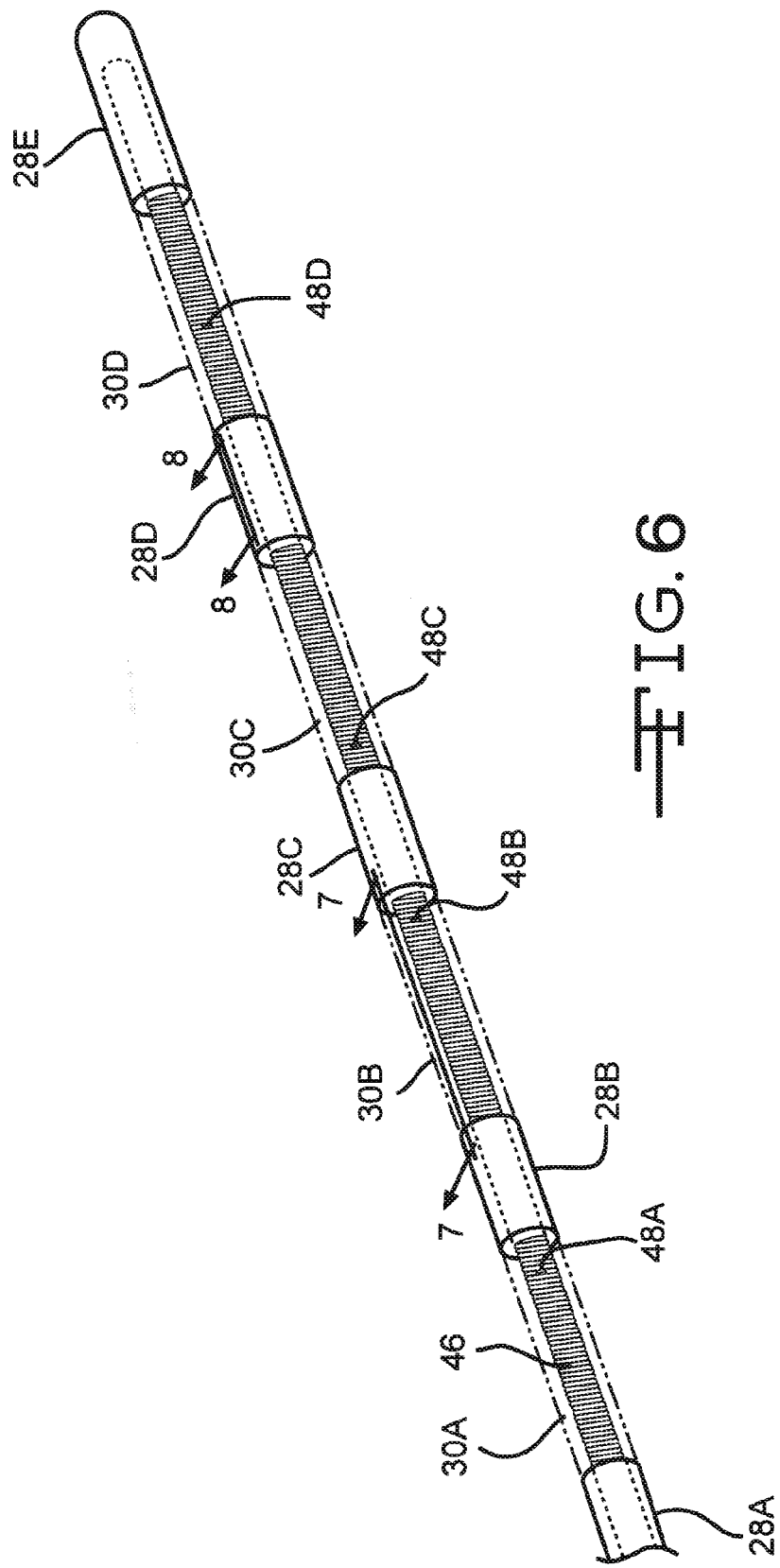

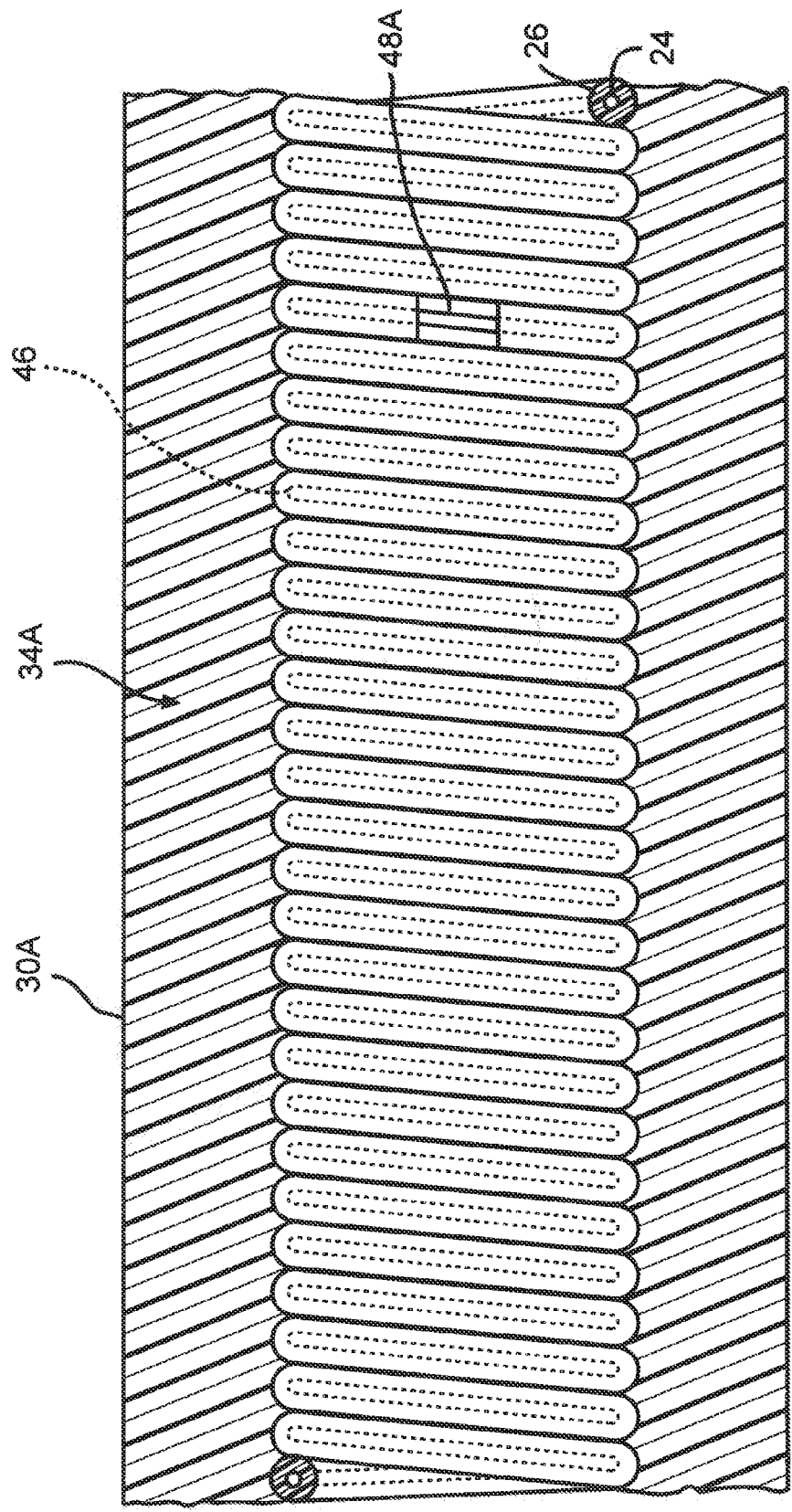

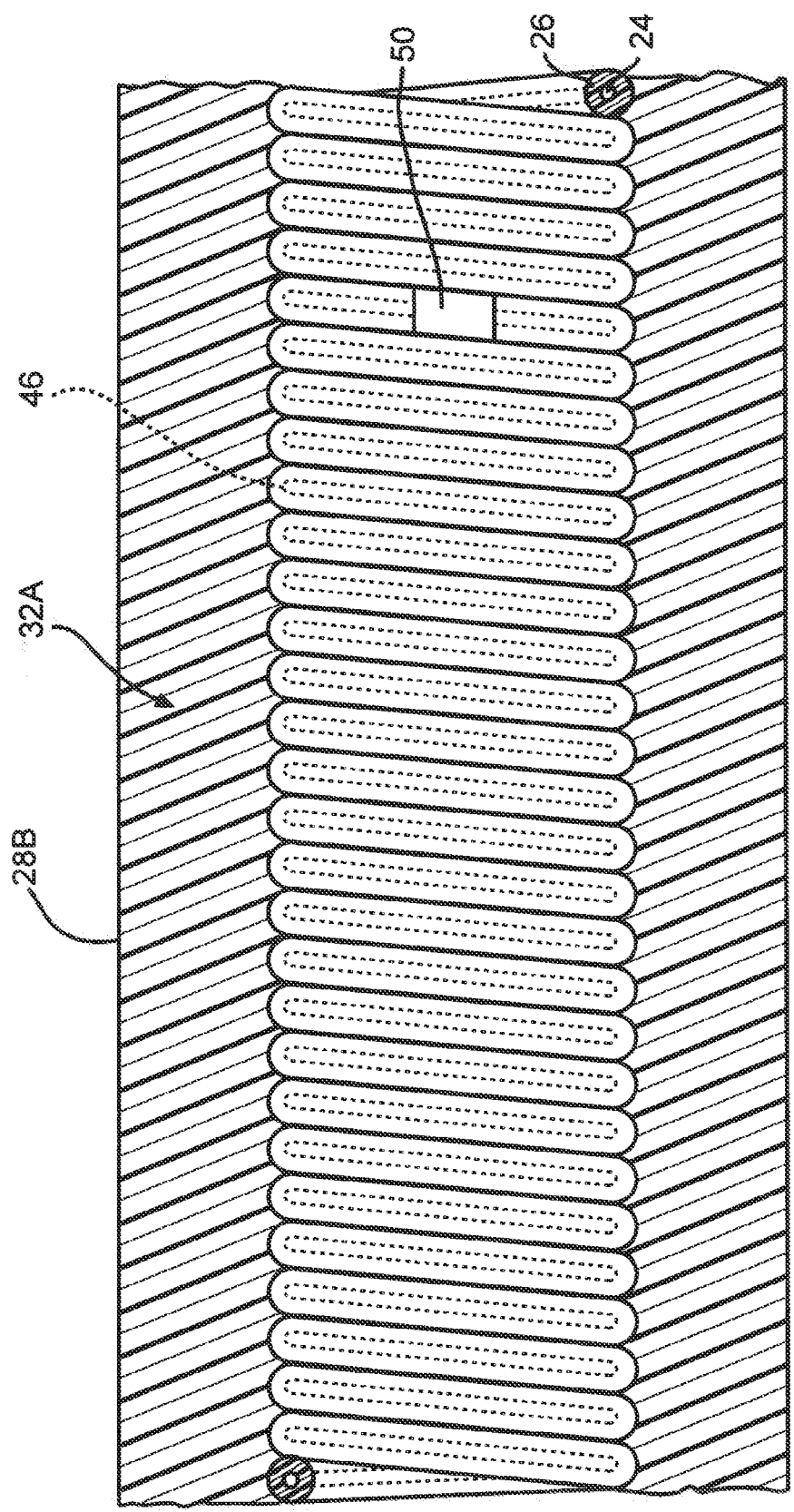

US 8,649,878 B2

TEMPORARY STIMULATION LEAD WITH POLYMER ELECTRODES AND METHOD OF MANUFACTURE

CROSS-REFERENCE TO RELATED APPLICATION

The present application claims priority from U.S. Provisional Application Ser. No. 61/218,498, filed Jun. 19, 2009.

BACKGROUND OF THE INVENTION

1. Field of the Invention

The present invention is related generally to medical stimulation leads. More specifically, the present invention is related to a temporary stimulation lead with polymer electrodes.

2. Background Art

Medical stimulation leads provide a means to deliver electrical energy from an implantable medical device such as a pacemaker or neurostimulator to stimulate body tissue. Such leads are complex devices that are designed with an intricate network of conductor wires and electrodes. Medical stimulation leads can be categorized as being either a permanent medical lead or a temporary medical lead. As the name implies, permanent medical stimulation leads are placed in the body for chronic use to provide continuous long-term stimulation to cardiac or neurological tissue. On the other hand, a temporary medical stimulation lead is designed for relatively short term use in the body. Permanent medical stimulation leads are designed for long term implantation of about 6 months or more and are typically constructed with more durability than temporary medical stimulation leads.

Before a permanent medical lead system is implanted, a temporary stimulation lead is used to screen potential patients for therapy effectiveness. This saves expense and minimizes the invasiveness of the procedure to the patient until it can be proven that the system will be efficacious. Previous prior art temporary leads provide monopolar stimulation in an effort to save size and expense. The present invention provides a cost effective multi-polar temporary lead with a small diameter which creates less trauma to the patient.

Polymeric materials have previously been used to construct medical stimulation leads. Such leads utilizing polymeric materials are disclosed in U.S. Pat. No. 7,225,035 to Brabec et al., U.S. Pat. No. 6,922,588 to Kranz et al. and U.S. Pat. No. 5,667,615 to Maurer et al.

Brabec et al. in the '035 patent discloses the use of conductive polymers such as carbon filled silicone, polyacetylene, polypyrrole and polyanaline for use as an electrode material. Such materials, as stated by Brabec, provide flexibility and allow the electrode to bend in the tight spaces of the coronary vasculature.

Kranz et al. in the '588 patent discloses the use of conductive polymeric materials that have been specially processed to produce an anisotropic electrical behavior. In the 588 patent, conductive polymeric materials such as polyacetylene, polyparaphenylene, polyphenylene sulfide, polyparaphenylvinylene, polypyrrole, polyfuran, polythiophen, polyphenylamine, polyethylenedioxythiophen-polystyrene sulfonate and polyacene, are processed to produce an electrically conductive medical lead (electrode line as stated by Kranz) designed to minimize electrical radial conduction and enhance electrical conduction along the lead's longitudinal axis. As Kranz states, in column 4, line 32 of the '588 patent, "By presetting the respective polymerisation and processing conditions which are to be adapted to the respective individual case involved, it is possible to ensure that the individual polymer chains of the intrinsically conductive polymer coaxially oriented in the longitudinal direction of the electrode line 12 and there is no conductivity worth mentioning in the radial direction." As will be discussed in more detail, the present invention is directed to the use of polymeric materials in electrodes where emission of electrical energy in a radial direction is desired.

Mauerer et al. in the '615 patent is directed to a vaginal electrode with alternating bands of conductive carbon filled silicone and non-conductive silicone rubber. Mauerer discloses an improved means of coupling electrical energy to the electrode through the use of mechanical tension to secure the lead wires to the polymeric electrodes of carbon loaded silicon rubber.

Unlike Mauerer, however, the temporary medical stimulation lead of the present invention utilizes a hydrophilic polymeric hydrogel material that acts as both an electrical stimulation electrode and a reservoir from which a therapeutic drug is eluted. Electrical energy is radially emitted from the hydrogel structure that provides therapeutic electrical stimulation to body tissue. In addition, a therapeutic drug can be emitted from the surface of the hydrophilic hydrogel material from which it is stored.

Furthermore, the present invention provides multipolar stimulation that provides increased control of the electrical stimulation as compared to monopolar prior art stimulation. In addition to the medical lead's simplified construction, the use of the conductive hydrophilic hydrogel material provides a cost effective means to stimulate tissue and elute therapeutic drugs that provide a pharmacological benefit.

SUMMARY OF THE INVENTION

The present invention comprises a medical device lead that utilizes a polymeric hydrophilic hydrogel material as the electrode structure of a temporary medical lead. The hydrophilic hydrogel electrode operates on the principal of ionic conduction. Salt ions that are diffused into the porous hydrophilic hydrogel structure act as electrical conductors that transfer electrical energy from the medical device to targeted body tissue. The hydrogel material also acts as a vehicle capable of eluting a therapeutic drug. The present invention comprises an elongated lead body having proximal and distal lead regions through which conductor wires extend through the lead body center from the proximal region to the distal region.

A series of individually insulated conductor wires contained within the implantable medical device extend the length thereof from the lead's proximal region to the distal region of the lead. The strands of conductor wires are bundled in a cable or coiled form for ease of manufacture.

The distal region of the lead is comprised of a series of alternating bands of electrically conductive and insulating polymers. The alternating conductive and insulating polymer bands comprising the lead's distal region wrap around the bundle of conductor wire strands. These alternating conduction and insulation polymer bands create a series of electrically isolated electrodes through which the medical device's electrical energy is transmitted to the targeted tissue. Each strand of conductor wire is electrically connected to a single hydrogel conduction band i.e., an electrode. The lead is designed to allow for the emission of positively and negatively charged electrical energy creating a multipolar lead in which electrical energy delivered through the hydrogel electrode is independently controlled by the medical device.

The conductive polymer bands are made from a hydrophilic hydrogel polymeric material that has been diffused with electrically conductive salt ions. These salt ions enable the flow of electrical energy via the migration of conductive ions within the material, thus creating an electrode in which electricity is conductable through the hydrogel material and radially emittable from the electrode surface for stimulating tissue that is in contact with the hydrogel electrode.

The insulation bands located on both sides of the conduction band serve to electrically isolate the hydrogel electrode bands of the present invention. In addition to preventing electrical shorting, the isolation bands enable the electrodes to operate and deliver electrical energy that is of an independent magnitude and polarity from each other.

The structure of the hydrophilic hydrogel material can also be loaded with a therapeutic drug that is eluted from the electrode surface providing a pharmacological treatment.

Therefore, the present invention is a temporary medical stimulation lead with electrodes made from a hydrophilic hydrogel material that provides both electrical stimulation and pharmacological treatment.

BRIEF DESCRIPTION OF THE DRAWINGS

FIG. 6 depicts a perspective view of the present invention with a coiled conductor wire embodiment.

FIG. 7 illustrates an enlarged cross-sectional view taken along line 7-7 of FIG. 6 of the present invention depicting a notched wire strand of the coiled conductor wire embodiment in the hydrogel electrode band.

FIG. 8 illustrates an enlarged cross-sectional view taken along line 8-8 of FIG. 6 of the present invention depicting a gap of space in an insulation band between a severed wire strand of the coiled wire embodiment.

DETAILED DESCRIPTION OF THE PREFERRED EMBODIMENTS

Figure 1:
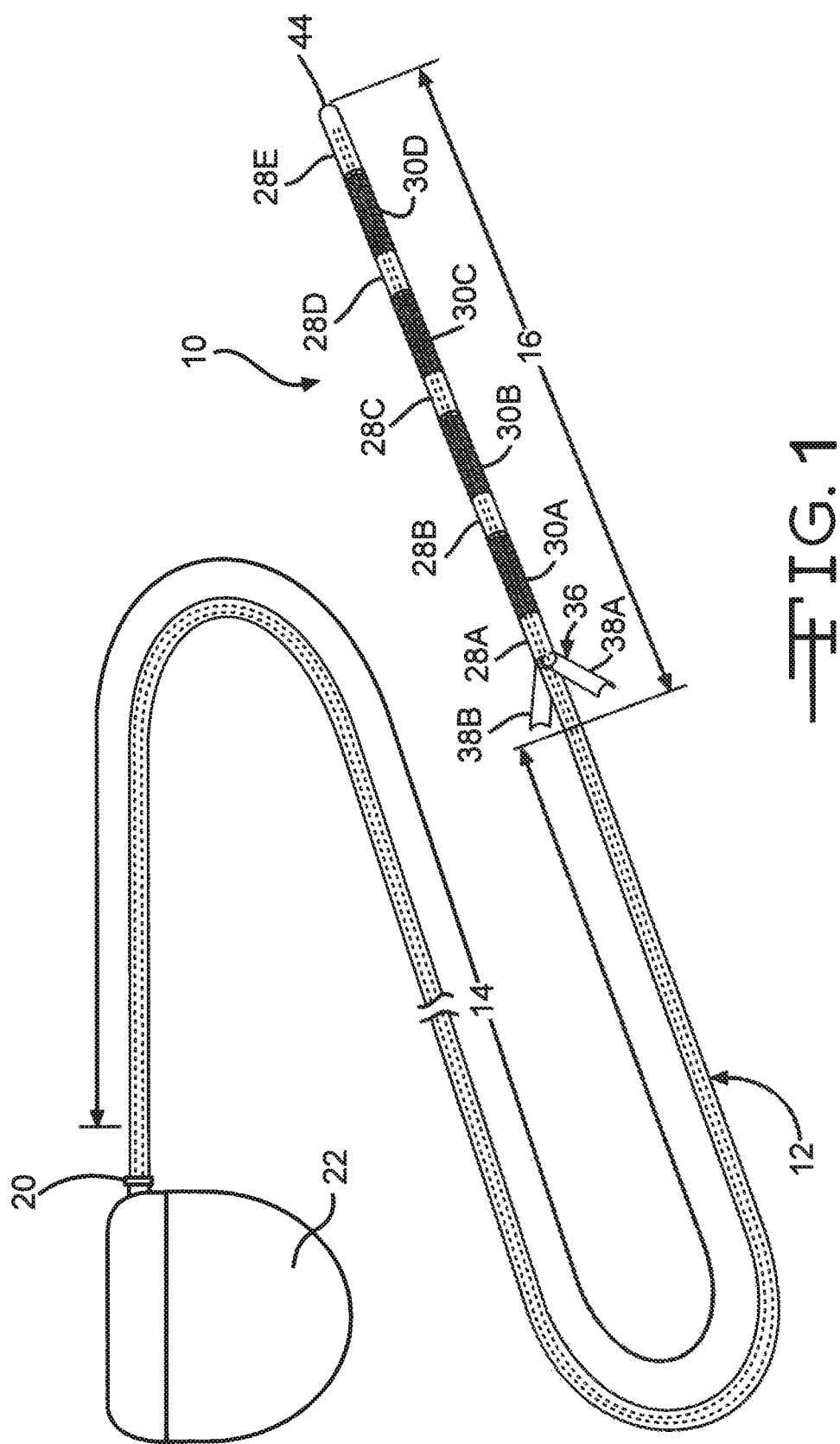
FIG. 1 shows a perspective view of the present invention of a temporary medical lead system.

Now referring to the figures, FIG. 1 shows a perspective view of the present invention of a medical lead 10 that is intended for temporary implantation in a patient. The lead of the present invention is designed to provide, if desired, both electrical stimulation and pharmacological treatment to cardiac, neurological or other targeted tissue.

Figure 2:
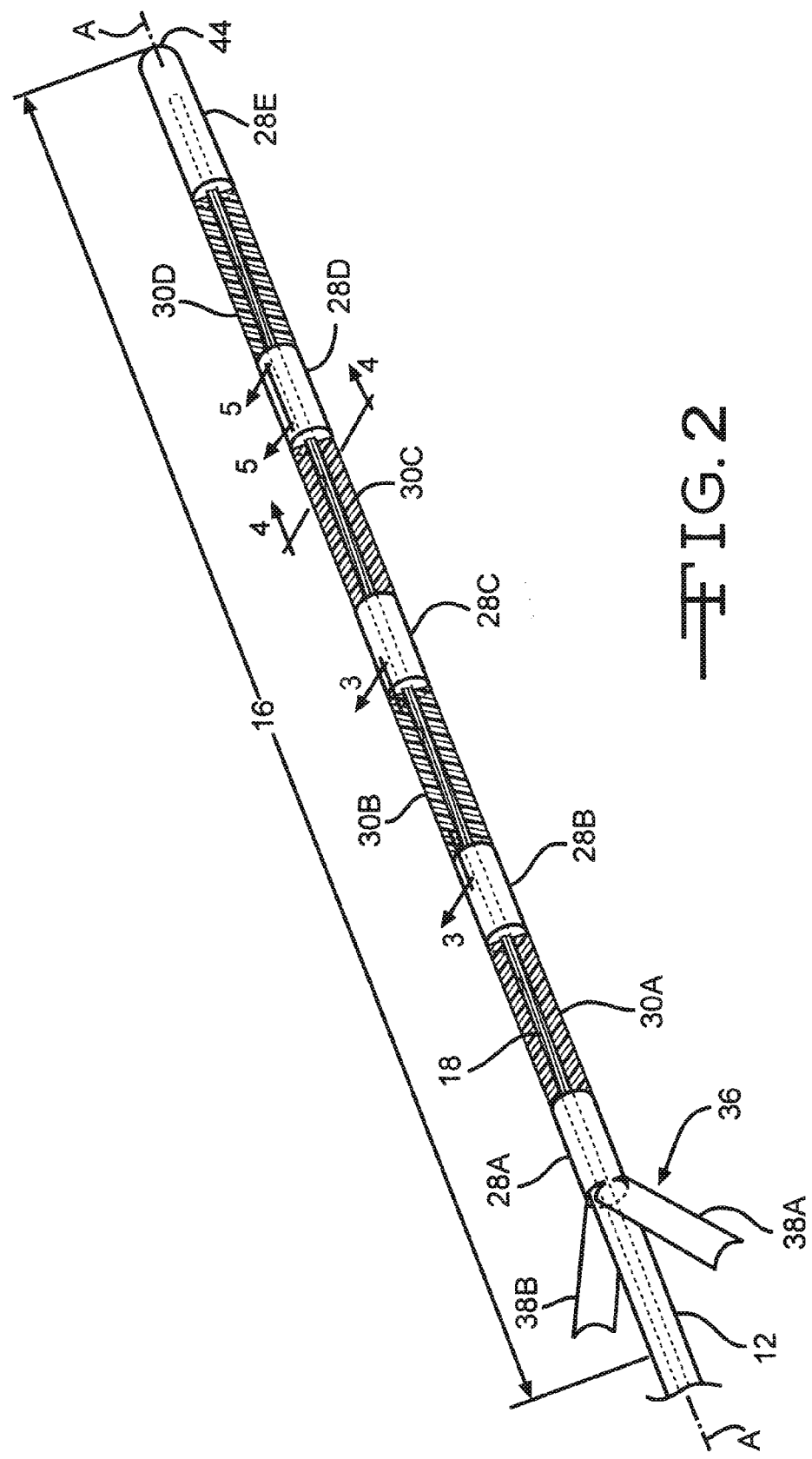
FIG. 2 shows an enlarged perspective view of the distal region of the present medical lead.

The medical lead 10 comprises a flexible, elongated lead body 12 having a thickness and a length comprising a lead proximal region 14 and a lead distal region 16. As shown in FIG. 2, a longitudinal axis A-A extends along the lead body 12. In a preferred embodiment, the lead body 12 has a diameter that ranges from about 1 mm to about 6 mm and a length that ranges from about 15 cm to about 200 cm. A plurality of individual electrically insulated conductor wires 18 reside in the lead body 12. The conductor wires 18 extend from the lead proximal region 14 to the lead distal region 16 along the longitudinal axis A-A. The portion of the conductor wires 18 located at the lead proximal end 20 are connectable to a medical device 22 such as the one shown in FIG. 1.

In a preferred embodiment, there are a total of sixteen insulated conductor wires 18, each made from a wire strand 24 of a preferred metallic material such as MP35N, titanium, stainless steel or silver cored wire. Surrounding each wire strand 24 is an electrically insulative coating 26, preferably made of polyurethane, polyimide, silicone, polytetrafluoroethylene, ethylene tetrafluoroethylene, fluoropolymers and combinations thereof. The insulative coating 26 preferably extends along the entire length of each of the wire strands 24. Alternately, these insulated conductor wires 18 could be made from a conductive polymer such as polypyrrole or carbon filled silicone. Although it is preferred that the lead body 12 contain sixteen insulated conductor wires 18, the present invention could be made with more or a fewer number of insulated conductor wires 18.

Within the lead distal region 16 are a series of alternating insulation bands 28 and conduction bands 30, as shown in FIGS. 1, 2, and 6. Both the insulation bands 28 and conduction bands 30 are discrete bands with a length and thickness that reside along longitudinal axis A-A, in which the insulated conductor wires 18 pass through. In a preferred embodiment, the insulation bands 28 have a solid insulation body 32 and the conductor bands 30 have a solid conductor body 34 through which the insulated conductor wires 18 tunnel therethrough. As shown in the cross sectional view in FIG. 4, four insulated conductor wires 18A, 18B, 18C and 18D extend along the length of the conductor band 30A. Conductor band body 34A surrounds insulated conductor wires 18A, 18B, 18C and 18D. Alternatively, both the insulation bands 28 and conductor bands 30 can be constructed with a hollow passageway that allows space for the insulated conductor wires 18.

In a preferred embodiment, the insulation bands 28 have a preferred diameter of about 1.5 mm, a length of about 1 cm to about 10 cm and a thickness therewithin. It is preferred that the conduction bands 28 have a diameter of about 3 mm, a length of about 1 cm to about 10 cm and a thickness therewithin. However, the diameter of both the insulation and conductive bands can range from about 1 mm to about 6 mm.

Also shown in FIG. 1 is an anchor structure 36 comprised of two protruding prongs 38A, 38B. The anchor structure 36 is designed so that the medical lead 10 can be easily advanced distally into position, but proximal movement is restricted due to the protruding prongs 38A,38B. Prongs 38A,38B are composed of a biocompatible insulative polymer such as silicone rubber or polyurethane that provide a rigid yet flexible structure. The prongs 38A,38B are attached to the exterior of the lead body 12 at the proximal end of the lead distal region 16 in such a manner that each prong 38A,38B is oriented at an angle of about 20 to about 40 degrees from longitudinal axis A-A with their terminal ends pointed outwardly toward the lead proximal region 14. The prongs 38A, 38B of the anchor structure 36 flex downwardly toward the lead body 12. Each of the prongs 38A,38B are curved with a concave backside that matches the curved contour of the lead body 12.

FIG. 2 illustrates an enlarged view of the lead distal region 16. The lead distal region 16 comprises of a series of alternating insulation bands 28A, 28B, 28C, 28D and 28E and conduction bands 30A, 30B, 30C and 30D, which act as the electrodes of the lead. Extending through the center of these bands 28,30 are a plurality of individually insulated conductor wires 18. In a preferred embodiment, there is one more insulation band 28 than conduction band 30, and the number of conduction bands 30 equals the number of insulated conductor wires 18. For example, it is preferred that there are sixteen conductor wires 18 and sixteen conduction bands 30, each conductor wire 18 being in electrical contact with the hydrogel material of a respective conductor band 30. Although it is preferred that the number of insulation wires 18 equals the number of conductor bands 30, it is contemplated that multiple insulation wires 18 could be electrically connected to a single conduction band 30 to provide redundancy and a more robust medical lead 10.

In a preferred embodiment, conduction bands 30, including the conductor band body 34, are composed of an electrically conductive hydrophilic hydrogel polymer such as a thermoplastic polyurethane elastomer which is sold under the trade name of Techophilic and manufactured by Lubrizol Advanced Materials of Wickliffe, Ohio.

The hydrophilic hydrogel polymer is designed to absorb a liquid such as a saline solution. Salt ions from the saline solution incorporate into the porous hydrogel material structure to provide a means for electrical conduction within the hydrogel material of the conductor band. Prior to use, the medical lead 10 is submerged in saline where it is allowed to soak for about 10 minutes to about 3 hours. That is so the conduction bands 30 have a sufficient amount of saline and electrically conductive salt ions diffused in the hydrophilic polymer hydrogel structure.

It is possible, however, that the medical lead 10 could be inserted into the body without previously soaking the lead in saline. In this situation, the operation of the medical lead 10 would rely upon the diffusion of ions present in the body into the hydrogel material to provide electrical conductivity.

In addition, a therapeutic drug can be loaded within the porous hydrophilic structure of the hydrogel material. Prior to insertion of the lead into a body tissue, the therapeutic drug is incorporated into the structure of the hydrogel by either soaking the hydrogel material in the therapeutic drug or injecting the hydrogel material with the therapeutic drug, such as with a needle or syringe. The therapeutic drug is then sequentially eluted from the porous structure of the hydrogel material when the conduction band 30 is located at a targeted site. This elution of a therapeutic drug provides a pharmacologic benefit in addition to providing electrical stimulation. Therapeutic drugs are eluted from the hydrogel material of the conductor band 30 to prevent and combat infection, and control pain among other therapeutic benefits. Suitable therapeutic drugs include, but are not limited to, beclamethason, baclofen, dexamethosone, coumadin, heparin, their derivatives and the like.

In a preferred embodiment, the insulation bands 28 are made from a biocompatible electrically insulative material such as polyurethane, polyimide, silicone, polytetrafluoroethylene, Ethylene tetrafluoroethylene, fluoropolymers and combinations thereof.

Figure 3:
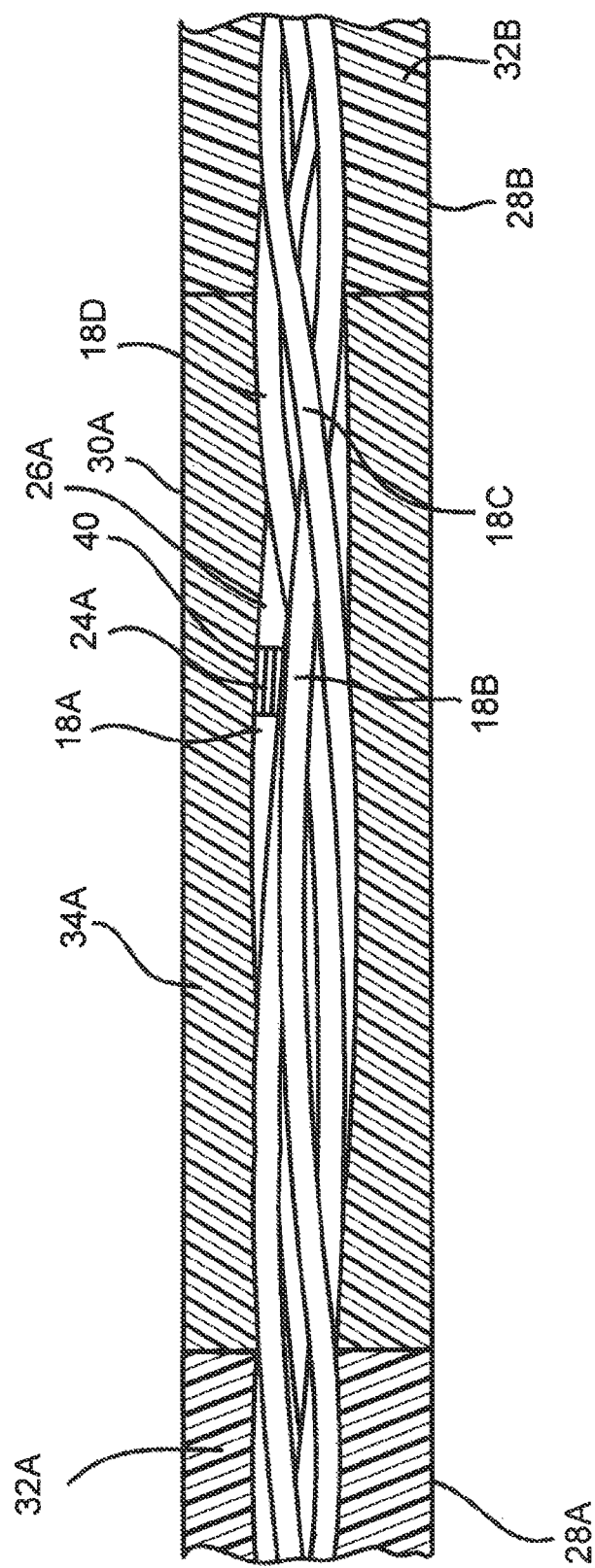
FIG. 3 illustrates an enlarged cross-sectional view taken along line 3-3 of FIG. 2 of the present invention depicting the notched conductor wire in the hydrogel electrode band.

FIG. 3 is an enlarged cross-sectional view of conductor band 30A. As shown in the figure, the insulation on the conductor wire 18A is notched 40, thus revealing a portion of bare conductor wire 24A. The amount of removed insulation 26A could be a relatively small spot or it could have sufficient length in the shape of a band.

Exposing the bare conductor wire 24A to the hydrogel material creates an electrical connection between the wire 24 and conductor 30. There is one notched insulated conductor wire 18 per corresponding conductor band 30. By limiting the conductor band 30 to one corresponding notched insulated conductor wire 18, a multichannel electrode medical lead is created in which each conductor band 30 (i.e. electrode) is independently controllable by the medical device 22. Each conductor band 30 is electrically connected to a single insulated conductor wire 18 and establishes an independently controllable electrical channel between the medical device 22 and conductor band 30, i.e. electrode.

For example, the present invention may be configured in which a first conductor band 30A is connected to a first insulated conductor wire 18A via a notch 40 in the insulation 26A of the first wire 24A, thereby creating a first channel, a second electrode band 30B is connected to a second insulated conductor wire 18B via a notch 40 in the insulation 26B of the second wire 24B, thereby creating a second channel, and so forth until all the conductor bands 30 are connected to insulated conductor wires 18 via at least one notch 40 in the insulation 26 of a respective conductor wire 24, thereby creating independent channels. Therefore, the medical device 22 is capable of independently controlling the amount of electrical energy being transmitted to each independent conductor band 30.

Although the lead may be produced with any number of electrode channels, it is preferred that the lead have an even number of electrode channels to allow for a balance of positive and negative electrical charges. The multiple independent channels of the device make it possible for the lead of the present invention to be multi-polar. A multi-polar lead is one in which both positive and negative electrical energy is conducted and emitted through the conductor bands 30, i.e. electrodes of the medical lead 22.

The insulated conductor wires 18 are electrically terminated within the insulation bands 28. After the insulated conductor wire 18 has been notched 40, exposing the bare wire 24 and therefore creating an electrical connection to the conductor band 30, it is preferably cut or severed the wire at the next adjacent distal insulation band 28. In other words, a conductor wire 18 is preferably terminated in the next insulation band 28 that is distal to the conductor band 30 radially aligned with the notch 40 in that particular wire 18. This construction is primarily one of ease of manufacturability. Instead of constructing the lead from conductor wires 18 of different lengths corresponding to the axial position of their respective conductor bands 30, all of the wires forming the cable or coil, and the like, are of the same length. Then, each wire 24 has its insulation 26 notched 40 in alignment with its conductor band 30 and cut in alignment with the next distal most insulation band 28. The severed distal portions of each wire 24 are left in the lead even though they are no longer electrically connected to anything. This facilitates ease of manufacturability.

Alternatively, the insulated conductor wire 18 can be terminated by ending the insulated conductor wire 18 in the distal insulation band 28.

Figure 4:
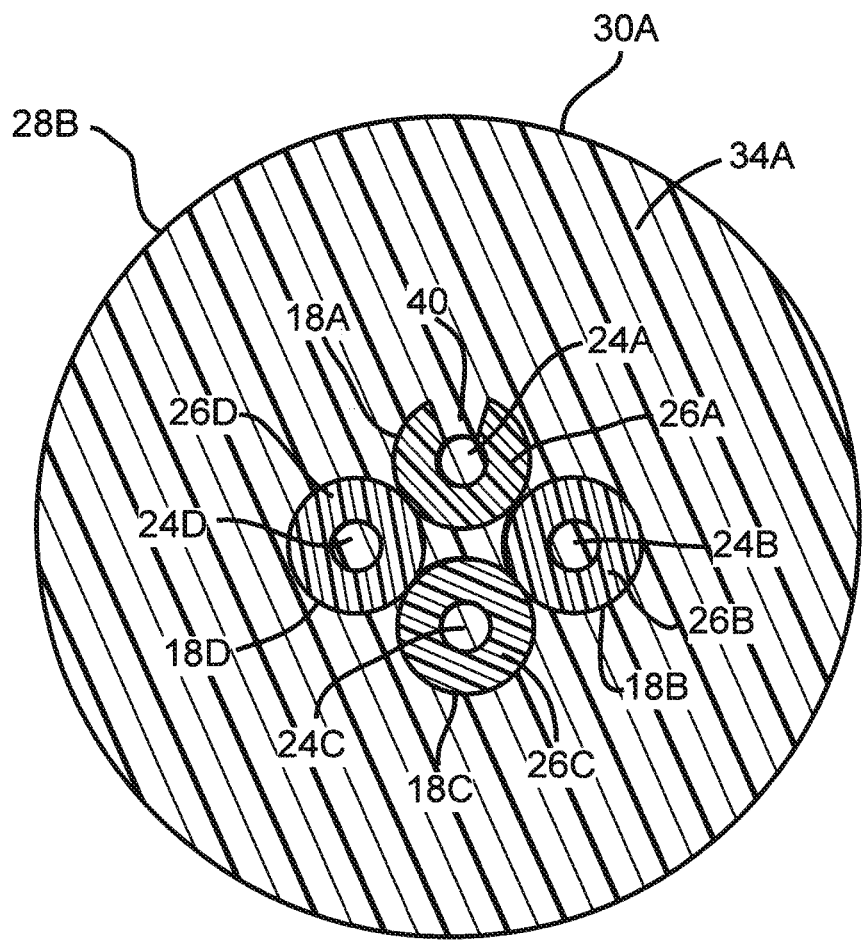
FIG. 4 depicts a cross sectional view taken along line 4-4 illustrating the notch in the insulation of the conductor wire strand in the electrode band.

FIG. 4 shows a cross sectional view, taken along line 4-4 of the conductor band 30A. As the figure shows, a series of four insulated conductor wires 18A, 18B, 18C and 18D are encased in the hydrogel material which comprises the conductor body 34A. Each of the conductor wires 24A, 24B, 24C and 24D has a sheath of insulation material 26A, 26B, 26C and 26D surrounding the diameter of the wire 24.

Figure 5:
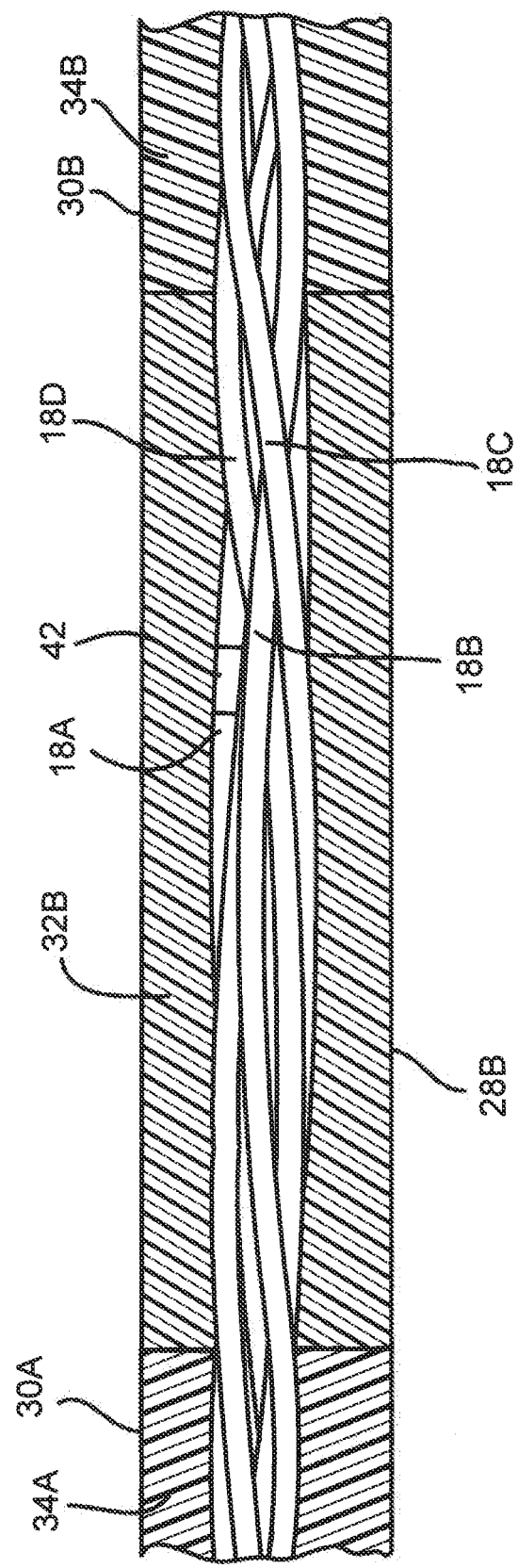
FIG. 5 illustrates an enlarged cross-sectional view taken along line 5-5 of FIG. 2 of the present invention depicting a severed conductor wire strand in the insulation band.

As shown in FIG. 5, in a preferred embodiment, there is a gap 42 in which the insulated conductor wire 18A is severed in two distinct wire halves in an insulation band 28B. A laser is preferably used to ablate and sever the wire 18. The insulated conductor wires 18 are terminated to prevent electrical shorting at the lead distal end 44.

As shown in FIG. 6, in an alternate embodiment, insulated conductor wires 18 can be bundled in the form of a coil. As previously shown in FIG. 3 in which the insulated conductor wires 18 are bundled in the form of a cable, each of the coiled conductor wires 46 in the alternate embodiment form has a coiled conductor notch 48. The coiled conductor wires 46 are terminated in the insulation bands 28. It should be noted that the insulated conductor wires 18 in the present invention are not limited to bundling in the form of a coil or cable but could also be bundled in other forms such as a braid or as a insulated straight conductor wire 18.

FIG. 7 illustrates an enlarged cross-sectional view taken along line 7-7 of FIG. 6. This drawing shows a notch 48A in the insulation coating 26 of the coiled wire embodiment 46 of the present invention. Similarly to the cable embodiment, shown in FIG. 3, a section of insulation coating 26 is removed from the coiled conductor wire 46, exposing an area of bare conductor wire 24. This exposed coiled conductor wire 24 forms an electrical connection path to the conductive hydrogel material of the conduction band 30A.

FIG. 8 illustrates an enlarged cross-sectional view taken along line 8-8 of FIG. 6. This drawing shows a gap 50 between two portions of a coiled conductor wire 46. Similar to the cable embodiment shown in FIG. 5, in a preferred embodiment, a coiled conductor wire 46 is electrically terminated by severing the wire 46 in two. As in the cabled wire embodiment, each coiled conductor wire 46 is electrically terminated in the insulation band 28. Once the insulation of the coiled conductor wire 46 is notched 48, exposing the bare coiled conductor wire it is then electrically terminated in the next distal insulation band 28.

In a preferred embodiment, the medical device lead 10 is constructed by first twisting the insulated conductor wires 18 in a cable or coiled form. The number of individual insulated conductor wires 18 corresponds to the number of conductor bands 30, i.e., electrodes. For example, four insulated conductor wires 18 correspond to four conductor bands 30, i.e. electrodes, eight insulated conductor wires 18 correspond to eight conductor bands 30, i.e. electrodes, and so forth.

Second, the wire insulation material 26 is removed from the conductor wires 18. Preferably a laser is used to ablate the insulation to create a bare, uninsulated spot on the conductor wire 18. Third, alternating tubes of the polymeric hydrogel conductor tubing and polymeric insulation tubing are placed over the insulated conductor wires 18, whether in a cabled or coiled form.

As previously mentioned, these insulation and conductor tubes can either be solid or hollow. When solid tubes are used, the insulated conductive wires 18 are bored through the material. When using coiled conductor wires 46, it is preferred that a mandrel be placed through the center of the coil. Tubes to provide added stiffness and act as a stylet can also be located in the center of the coil.

In a preferred embodiment, tubes of the polymeric insulation material are placed before and after the conductive tubes to provide electrical insulation and create electrically isolated conductor bands 30.

Third, heat shrink tubing is placed over the assembly and heat treated at about 200° C. to about 300° C. for about 30 to about 300 minutes. This heat treatment fuses the assembly of insulated conductor wires 18, and conductor and insulation tubes together, thereby creating intimate contact between the various areas of bare conductor wire 24 and conduction band material. Heat treatment also seals the alternating conductive and insulation tube segments together. Therefore, the alternating series of insulation bands 28 and conductor bands 30 are created.

Prior to use, the medical lead 10 is soaked in a bath of saline to transfer salt ions of the saline solution into the hydrogel structure of the conductor bands 30. It is preferred that the medical lead 10 be soaked in the saline bath for about 10 minutes to about 60 minutes. Additionally, the conductor bands 30 of the medical lead 10 can be soaked in or injected with a single therapeutic drug or combination of therapeutic drugs.

In that manner, the present medical stimulation lead is provided. The lead is capable of providing electrical stimulation and or pharmacological treatment when used in conjunction with a medical procedure intended to beneficially affect a body tissue.

What is claimed is:

1. A medical lead configured to provide electrical stimulation to body tissue, the medical lead comprising:
   a) at least one conductor band composed of a hydrophilic thermoplastic polyurethane elastomer, the conductor band having a conductor band lumen extending along a conductor band length from a conductor band proximal end to a conductor band distal end; and
   b) at least one insulated conductor wire having a conductor wire length extending from a proximal region of the lead, through the conductor band lumen to a distal region of the lead;
   c) wherein the at least one conductor wire is provided with a notch in its insulation to thereby expose an uninsulated conductor wire length with at least a portion of the notch being radially aligned with the conductor band, and
   d) a heat treated heat shrink tubing covering the at least one conductor band to thereby force the conductor band into an intimate electrically conductive contact relationship with at least a portion of the uninsulated conductor wire length at the notch somewhere between the conductor band proximal and distal ends thereof.

2. The medical lead of claim 1 wherein the at least one conductor wire has a cut that is distal of the notch and that terminates electrical conductivity at the cut.

3. The medical lead of claim 1 wherein electricity is conductible through the at least one conductor band through an ionic conduction.

4. The medical lead of claim 1 wherein electricity is conductible through the at least one conductor band through ionic conduction provided by salt ions in a saline solution infusible into the conductor band.

5. The medical lead of claim 1 wherein the hydrophilic thermoplastic polyurethane elastomer is loaded with a therapeutic drug selected from the group consisting of beclamethason, baclofen, dexamethosone, coumadin, heparin, their derivatives, and combinations thereof.

6. A medical lead configured to provide electrical stimulation to body tissue, the medical lead comprising:
   a) at least a first and a second conductor bands composed of a hydrophilic thermoplastic polyurethane elastomer, the first and second conductor bands each having a conductor band lumen extending along a conductor band length between and to respective conductor band proximal and distal ends;
   b) at least three insulator bands, each insulator band having an insulator band lumen extending along an insulator band length, wherein one of the conductor bands is disposed intermediate two of the insulator bands to thereby insulate the first and second conductor bands from each other; and
   c) at least a first insulated conductor wire and a second insulated conductor wire, each having respective first and second conductor wire lengths extending from a proximal region of the lead, through the conductor band lumens and the insulator band lumens to a distal region of the lead,
   d) wherein the first and second conductor wires are provided with respective first and second notches in their insulation to thereby expose first and second uninsulated conductor wire lengths with at least a portion of the first and second notches being radially aligned in a perpendicular orientation to a longitudinal axis of the respective first and second conductor band lengths, and e) a heat treated heat shrink tubing covering the first and second conductor bands spaced from each other by the at least three insulator bands to thereby force the first and second conductor bands into an intimate electrically conductive contact relationship with the first and second uninsulated conductor wire lengths at theft notches somewhere between the respective first and second conductor band proximal and distal ends thereof.

7. The medical lead of claim 6 wherein at least the first and the second conductor wires each have a cut that is distal of the respective notch and that terminates electrical conductivity at the cut.

8. The medical lead of claim 7 wherein the cut is radially aligned with one of the respective first and second insulator bands.

9. The medical lead of claim 6 wherein the at least three insulator bands are composed of a biocompatible electrically insulative material selected from the group consisting of polyurethane, polyimide, silicone, polytetrafluoroethylene, Ethylene tetrafluoroethylene, fluoropolymers and combinations thereof.

10. The medical lead of claim 6 wherein the insulator band length of each of the insulator bands is from about 1 cm to about 10 cm and the diameter of each of the insulator bands is from about 1 mm to about 6 mm.

11. The medical lead of claim 6 wherein the conductor band at least the first and second length of conductor bands is from about 1 cm to about 10 cm and the diameter of at least the first and second conductor bands is from about 1 mm to about 6 mm.

12. The medical lead of claim 6 wherein electricity is conductible through at least the first and the second conductor bands through an ionic conduction.

13. The medical lead of claim 12 wherein the ionic conduction is providable by salt ions in a saline solution that is infusible into at least the first and the second conductor bands.

14. The medical lead of claim 6 wherein the hydrophilic thermoplastic polyurethane elastomer is loaded with a therapeutic drug selected from the group consisting of beclamethasone, baclofen, dexamethosone, coumadin, heparin, their derivatives, and combinations thereof.

15. The medical lead of claim 6 wherein the insulation of the conductor wires is selected from the group consisting of polyurethane, polyimide, silicone, polytetrafluoroethylene, ethylene tetrafluoroethylene, fluoropolymers and combinations thereof.

16. The medical lead of claim 6 configured to be connectable to a medical device selected from the group consisting of a pacemaker, defibrillator, and a neurostimulator.

17. A medical lead configured to provide electrical stimulation to body tissue, the medical lead comprising:

a) at least a first and a second conductor bands composed of a hydrophilic thermoplastic polyurethane elastomer, the first and second conductor bands each having a conductor band lumen extending along a conductor band length between and to respective conductor band proximal and distal ends;

b) at least three insulator bands, each insulator band having an insulator band lumen extending along an insulator band length, wherein one of the conductor bands is disposed intermediate two of the insulator bands to thereby insulate the first and second conductor bands from each other; and c) at least a first insulated conductor wire and a second insulated conductor wire, each having respective first and second conductor wire lengths extending from a proximal region of the lead, through the conductor band lumens and the insulator band lumens to a distal region of the lead, d) wherein the first and second conductor wires are provided with respective first and second notches in their insulation to thereby expose an uninsulated conductor wire length that is radially aligned with at least a portion of the respective first and second conductor band lengths, and e) a heat treated heat shrink tubing covering at least the first and second conductor bands spaced from each other by the at least three insulator bands to thereby force the first and second conductor bands into an intimate electrically conductive contact relationship with at least a portion of the first and second uninsulated conductor wire lengths at theft notches somewhere between the respective first and second conductor band proximal and distal ends thereof.

18. The medical lead of claim 17 wherein at least the first and the second conductor wires each have a cut that is distal of the respective notch and that terminates electrical conductivity at the cut.

19. The medical lead of claim 18 wherein the cut is radially aligned with one of the respective first and second insulator bands.

20. The medical lead of claim 17 wherein electricity is conductible through at least the first and the second conductor band through an ionic conduction.

21. The medical lead of claim 17 wherein the at least three insulator bands are composed of a biocompatible electrically insulative material selected from the group consisting of polyurethane, polyimide, silicone, polytetrafluoroethylene, Ethylene tetrafluoroethylene, fluoropolymers and combinations thereof.

* * * * *

UNITED STATES PATENT AND TRADEMARK OFFICE
CERTIFICATE OF CORRECTION

| | | |
|---|---|---|
| PATENT NO. | : 8,649,878 B2 | Page 1 of 1 |
| APPLICATION NO. | : 12/818207 | |
| DATED | : February 11, 2014 | |
| INVENTOR(S) | : Swoyer | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this
Second Day of June, 2015

Michelle K. Lee
*Director of the United States Patent and Trademark Office*

UNITED STATES PATENT AND TRADEMARK OFFICE
CERTIFICATE OF CORRECTION

PATENT NO. : 8,649,878 B2 Page 1 of 1
APPLICATION NO. : 12/818207
DATED : February 11, 2014
INVENTOR(S) : John Swoyer It is certified that error appears in the above-identified patent and that said Letters Patent is hereby corrected as shown below:

Claims

Column 9, line 11 (Claim 6, line 34) delete "theft" and insert --their--

Column 9, line 32 (Claim 11, line 2) after the word "band" insert --length of--

Column 9, line 32 (Claim 11, line 2) after the word "second" delete the words "length of"

Column 10, line 33 (Claim 17, line 33) delete "theft" and insert --their--

Column 10, line 47 (Claim 20, line 3) delete "band" and insert --bands--

Signed and Sealed this
Fifteenth Day of March, 2016

Michelle K. Lee
*Director of the United States Patent and Trademark Office*